(12) United States Patent
Rosengart (10) Patent No.: US 11,013,489 B2
(45) Date of Patent: May 25, 2021

(54) DETECTION AND QUANTIFICATION OF BRAIN MOTION AND PULSATILITY

(71) Applicant: Axel Rosengart, Hackensack, NJ (US)

(72) Inventor: Axel Rosengart, Hackensack, NJ (US)

(73) Assignee: Axel Rosengart, Hackensack, NJ (US)

( * ) Notice: Subject to any disclaimer, the term of this patent is extended or adjusted under 35 U.S.C. 154(b) by 111 days.

(21) Appl. No.: 16/324,457

(22) PCT Filed: Aug. 7, 2017

(86) PCT No.: PCT/US2017/045771
§ 371 (c)(1),
(2) Date: Feb. 8, 2019

(87) PCT Pub. No.: WO2018/031477
PCT Pub. Date: Feb. 15, 2018

(65) Prior Publication Data
US 2019/0175141 A1    Jun. 13, 2019

Related U.S. Application Data (60) Provisional application No. 62/372,729, filed on Aug. 9, 2016.

(51) Int. Cl.
| | | |
|---|---|---|
| *A61B 8/08* | (2006.01) | |
| *A61B 8/00* | (2006.01) | |
| *A61B 5/318* | (2021.01) | |
| *A61B 5/1455* | (2006.01) | |
| *A61B 8/02* | (2006.01) | |

(52) U.S. Cl.
CPC ........ *A61B 8/0808* (2013.01); *A61B 5/14551* (2013.01); *A61B 5/318* (2021.01); *A61B 8/02* (2013.01); *A61B 8/08* (2013.01); *A61B 8/4477* (2013.01); *A61B 8/486* (2013.01);
(Continued)

(58) Field of Classification Search
CPC ..... A61B 5/0402; A61B 5/14551; A61B 8/02; A61B 8/08; A61B 8/0808; A61B 8/4227; A61B 8/4477; A61B 8/486; A61B 8/52; A61B 8/5284; A61B 8/543
See application file for complete search history.

(56) References Cited

U.S. PATENT DOCUMENTS

| | | | |
|---|---|---|---|
| 5,951,476 A | * | 9/1999 | Beach .................. A61B 8/0808 600/437 |
| 6,547,731 B1 | | 4/2003 | Coleman |

(Continued)

OTHER PUBLICATIONS

Dewarja, A. S. et al, "GPU engine enhances ultrasound-detected brain motion calculations", Embedded Computing Design, May 1, 2009. Accessed online at: http://embedded-computing.com/articles/gpu-brain-motion-calculations/.

(Continued)

*Primary Examiner* — Jonathan T Kuo
(74) *Attorney, Agent, or Firm* — Quarles & Brady LLP (57) ABSTRACT

The pumping of arterial blood into the cerebral spinal fluid (CSF) of a patient's brain creates cycle pressure undulations in the CSF and the brain itself. Brain injuries can create abnormal changes in this pressure waveform. Accordingly, the disclosed technology includes an ultrasound based device for monitoring this brain movement in the CSF ("pulsatility") to diagnose and monitor brain injury.

19 Claims, 4 Drawing Sheets

(52) U.S. Cl.
CPC .............. *A61B 8/52* (2013.01); *A61B 8/5284* (2013.01); *A61B 8/543* (2013.01)

(56) References Cited

U.S. PATENT DOCUMENTS

| | | |
|---|---|---|
| 6,695,784 B1 | 2/2004 | Michaeli |
| 2003/0013956 A1 | 1/2003 | Michaeli |
| 2007/0293760 A1 | 12/2007 | Schaafsma |
| 2009/0143656 A1 | 6/2009 | Manwaring |
| 2010/0204589 A1 | 8/2010 | Swoboda |
| 2015/0359448 A1 | 12/2015 | Beach |

OTHER PUBLICATIONS

Wagshul et al. "The Pulsating Brain: A review of experimental and clinical studies of intracranial pulsality" Fluids and Barriers of the CNS, 2011, 8:5 https://fluidbarrierscns.biomedcentral.com/articles/10.1186/2045-8118-8-5.

International Search Report and Written Opinion for application PCT/US2017/045771, dated Dec. 11, 2017, 10 pages.

* cited by examiner

DETECTION AND QUANTIFICATION OF BRAIN MOTION AND PULSATILITY

FIELD

The present invention is directed to systems and methods for monitoring brain motion and pulsatility.

BACKGROUND

The following description includes information that may be useful in understanding the present invention. It is not an admission that any of the information provided herein is prior art or relevant to the presently claimed invention, or that any publication specifically or implicitly referenced is prior art.

The brain is located within the intracranial cavity where it floats in cerebrospinal fluids (CSF). Its anchoring connections to the skull are primarily arterial and venous vessels entering through the skull and branching throughout the brain, the brainstem column leaving the skull base and forming the spinal cord as well as groups of nerve endings (cranial nerves) exiting from the brainstem to the face.

Because the brain lacks firm anchoring structures, the pulsatile inflow of pulsatile, arterial blood volume entering the CSF-suspended brain induces well-defined brain pulsations which lead to predictable, reflective (expansion) movements of the brain within the intracranial cavity; most pronounced as a cyclic downward (rostrocaudal) movement during arterial systole. While under physiologic conditions, arterial blood and reflective brain pulsations closely correlate, changes in brain tissue density or volume will restrict and distort the brain's normal movement response (pulsations) to systolic blood inflow.

Brain injury of any type and significance leads to brain tissue densities changes (i.e., commonly from swelling, blood, etc.). These density changes can be global, that is, involve most or all structures and regions of the brain as seen after cardiac arrest with a prolonged period of blood flow cessation to the brain, or regionally (focal), for example, occurring in patients with swelling of one brain hemisphere from a stroke or hematoma. As brain density changes invariably alter the brain's passive movement responses to the pulsating waves of arterial blood flow entering the brain monitoring for either focal or global changes in brain motion and pulsatility is useful for detection and progression of brain injury. Detecting such abnormalities has been attempted in some forms.

For example, insonation of brain arteries and parenchyma has been performed using some technologies. As one example, Transcranial Doppler (TCD) ultrasound is employed to measure blood flow velocities within larger intracranial arteries (that is, within arterial segments located at the base of the skull and prior to entering into and branching throughout the brain tissue). The output of such TCD systems include calculations of blood flow velocities at different time points of the cardiac cycle (i.e., systolic and diastolic), derived means (i.e., mean velocity) and a parameter called "pulsatility index." This vascular PI is a calculated and frequently in the literature discussed and clinically used parameter which has no similarities with the herein disclosed "brain pulsatility."

The TCD-derived PI is a computed value derived from averages and ratios of systolic and diastolic mean velocities and it is obtained by insonating the intracranial arteries at the skull base level. The clinical value of TCD-derived PI is that systolic and diastolic flow velocities pattern of large (proximal) brain arteries close to the skull base (as only those can be examined by TCD) change to some degree with disturbances in brain density, i.e., from injury-induced swelling, as more downstream located, branched arterioles become increasingly compressed. Unfortunately, the vascular PI is not only an indirect measure of brain tissue changes but also subject to be influenced by a magnitude of unpredictable variables such as age-related rigidity or narrowing of the brain arteries and abnormal heart function. Therefore, the vascular PI is often a non-reliable marker for brain injury. Furthermore, obtaining PI measurements can be time consuming, requires technical expertise and is challenged by artifacts.

Cerebrospinal fluid (CSF) surrounds the brain parenchyma from within and around its structures and hence, arterial pulsations inducing not only successive brain pulsations but are also transmitted to the CSF. Therefore, CSF pulsation (=CSF waveform) and pressure (=absolute values) changes are common clinical parameters to diagnose and trend progression of brain injury. Unfortunately, to obtain CSF dynamics, invasive monitoring is needed such as inserting an external ventricular drainage (EVD) tube or pressure sensor through the skull bone and towards the center of the brain's fluid spaces which is commonly only indicated in moderate to severe brain injury patients cared for in the acute neuroscience setting.

Magnetic resonance imaging (MM) of the brain can detect brain and CSF motion and is currently used, among other uncommon indications, to understand treatment options for patients with (often congenital) CSF circulation abnormalities. However, this method provides only a brief snapshot of brain motion (minutes), has many limitations making it unrealistic for large-scale use (i.e., is restricted to dedicated imaging centers), and is very costly and cumbersome.

SUMMARY

The disclosed technology detects and quantifies in real-time blood flow-induced brain displacement and pulsatility. Comparisons of abnormal with normal (expected) brain movements can be made and used as a novel monitoring modality for brain injury.

Measured Pulsatility

In some examples, transcranial ultrasound is utilized to monitor the brain. However, in contrast to current transcranial ultrasound applications where either blood flow of intracranial arteries is measured (transcranial Doppler "TCD") or brain tissue is visualized (transcranial B— or 2D-Modes; i.e., during brain operations), the disclosed technology aims at quantifying the degree, orientation and pattern of brain movements. Such high resolution ultrasound quantification of tissue movements is a readily available imaging modality in medicine; for example, it is commonly performed to evaluate heart valve movements and referred to as "M" (Motion) Mode.

M-Mode imaging is useful in detecting and recording rapid movements as it provides very high temporal and spatial resolutions (1000 frames per second) of tissue motion along a single ultrasound beam. It is commonly used in cardiovascular ultrasound to study the movement of the myocardium and valves, to quantify volumes of chambers with changing dimensions or to exam the abnormalities of vessel walls. In these application examples, movements of a structure are measured by placing M-mode scan lines through the tissue area of interest and computing over time how the structure intersected by that line moves toward or away from the insonation probe. Additionally, in some current applications co-registration and correlation of M-mode with other signals such as arterial pulse wave, electrocardiogram (ECG) and respiratory excursions is obtained.

M-Mode technology to detect and quantify and analyze movements of the brain in one or more dimensions, however, does not exist. Accordingly, disclosed is technology for ultrasound insonation of the brain, that in some examples, is performed through defined skull access areas for ultrasound waves, namely through the thin bone windows of each temple (that is, right in front of the upper part of the earlobes) and through the foramen magnum (midline approach where the back of the neck meets the occipital skull bone). However, as some (lower) frequency ultrasound waves are capable to penetrate the skull bone in areas of regular thickness (that is, enter the brain tissue through the bone even outside of the above outlined 'ultrasound access points'), it is envisioned that brain insonating ultrasound can be also be applied at many different locations throughout the skull.

These three areas have been established as suitable ultrasound access points, for example, to insonate the brain arteries during TCD. Accordingly, disclosed is a headframe that allows simultaneous, hands-free operation of all three transducers (or other number of transducers) and each transducer acts simultaneously as ultrasound emitting and receiving unit. In some examples, the three transducers are synchronized and insonate the brain parenchyma with either continuous or intermittent pulse waves in the mega- or kilo-Hertz range. Furthermore, more than one insonation frequency and intensity maybe used simultaneously and at various angulations in order to obtained diagnostic interference/scatter patterns and to enhance the spatial and time resolution of brain movements.

In some examples, to generate three dimensional brain motion, the transducers emit and receive impulses in pre-defined on-off sequences and constellations. The pulsating brain will shorten (compress) or lengthen (relax) the emitted ultrasound waves dependent on the direction of its movement relative to the transducer emission unit (Doppler effect). The degree of wave length and amplitude changes reflected by the waves is extracted by the ultrasound processor and integrated to obtain graphic and numerical representations of brain motion. As these brain motions are caused by pulsation of arterial blood entering the brain we refer to them as brain pulsations and the obtained motion measurement as brain pulsatility.

In some examples, crystals or micro-transducers are employed to transmit and receive sound energy to measure changes in distance, directions and velocities between two or more pairs of crystals positioned around the skull. Such digital sonomicrometers (that is, ultrasound-based timing devices) can transmit from one or more crystals ultrasound bursts to multiple receivers and hence, generate a 2- and 3-dimensional display of brain motion. Specifically, such system can measure many, i.e., 496 dimensions between 32 crystals. The data sampling rate can range from 16 Hz to 1600 Hz and is user-adjustable. Each measurement has a relative error (dynamic resolution) of 0.024 mm however the resolution can be optionally enhanced to 0.0124 mm (12.4 um) and hence are capable of distinguishing and monitoring various brain pulsation forces. Furthermore, digital signals from such sonomicrometers can be time-locked with analog signals from pressure (blood, brain and/or thoracic pressures, among others), arterial and venous flow, or various other transducers. Brain pulsation measurements using the sonomicrometry approach can use commercial off-the-shelf diagnostic ultrasound readers to achieve multi-access wireless telemetry with millimeter-sized sonomicrometry crystal transducers. In this scenario sonomicrometry crystals transmit data using different modulation and coding techniques. In some examples, sonomicrometric crystals can be implanted into the brain tissue or connected to invasive brain monitoring devices to obtain a continuous, reliable telemetry link.

Estimated Pulsatility

In some examples, measured brain pulsatility will be compared with simultaneously obtained real-time arterial flow waveforms (e.g., obtained via a coin-size, patch-on transducer over the internal carotid artery at its position under the jaw or over the wrist area). In other examples, brain M-Mode can be timed and correlated alongside with ECG or respiratory pressure waveforms. This comparison facilitates patient and situational specific assessments by comparing expected brain pulsatility (based on the estimated arterial flow pattern of a patient at the time point of examination) and measured (obtained) brain pulsatility. Such discrepancies between expected and measured brain pulsatilities can be used, for example, to indicate further monitoring or work up for the presence of brain injury.

In support of the conceptual feasibility of the disclosed invention is the observation that intraoperative inspection of the injured brain during neurosurgical procedures can reveal visible problems with brain pulsations. For example, after operative skull opening and splitting of the dura (craniotomy with durotomy) in a patient with a brain hematoma, initially a non-pulsating or minimally pulsating brain is found. After hematoma evacuation and removal of the mass effect the brain relaxes and starts to pulsate again. The disclosed technology aims at translating such clinical observations into a standardized, noninvasive and safe technique to quantify and monitor progression of injury based on ultrasound-tracked brain pulsatility changes.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

The pumping of arterial blood into and through the brain creates reflective, cyclic movements of the brain tissue which expand, relax and change the brain positions in predictable ways. Brain injury leads to tissue density changes which depending on the location and extend of the brain injury affects restricted parts or of the brain. As a result the arterial waveform-induced reflective, cyclic movements of the injured brain tissue become abnormal and the disclosed technology includes an ultrasound-based device for monitoring, trending and categorizing brain movements ("or pulsatilitions") to diagnose and monitor brain injury.

In some examples, the device includes two ultrasound transducers placed on the temples, and one placed on the foramen magnum where the back of the neck meets the occipital skull bone. The three transducers are synchronized and emit either continuous or intermittent pulse waves in the megahertz or kilohertz range. The degree of wavelength and amplitude changes in the reflected waves are extracted and processed by the ultrasound processor to output graphical and numerical representations of the brain motion. Simultaneous emissions of more than one ultrasound frequency by the transducers may be used to amplify pulsatility detection, i.e., to delineate and detect motion differences within sub-compartments of the brain.

In some examples, these actual, real-time pulsatility measurements can be compared to expected pulsatility and flow measurements derived from a transducer placed on the patient's carotid artery under the jaw. For instance, the arterial flow pattern may be derived from the transducer on the carotid artery, which may then be processed to determine expected brain pulsatility (e.g., based on data from healthy patients). Then, if the system identifies discrepancies between measured and expected brain pulsatility, the patient may be flagged for potential brain injury.

Figure 1:
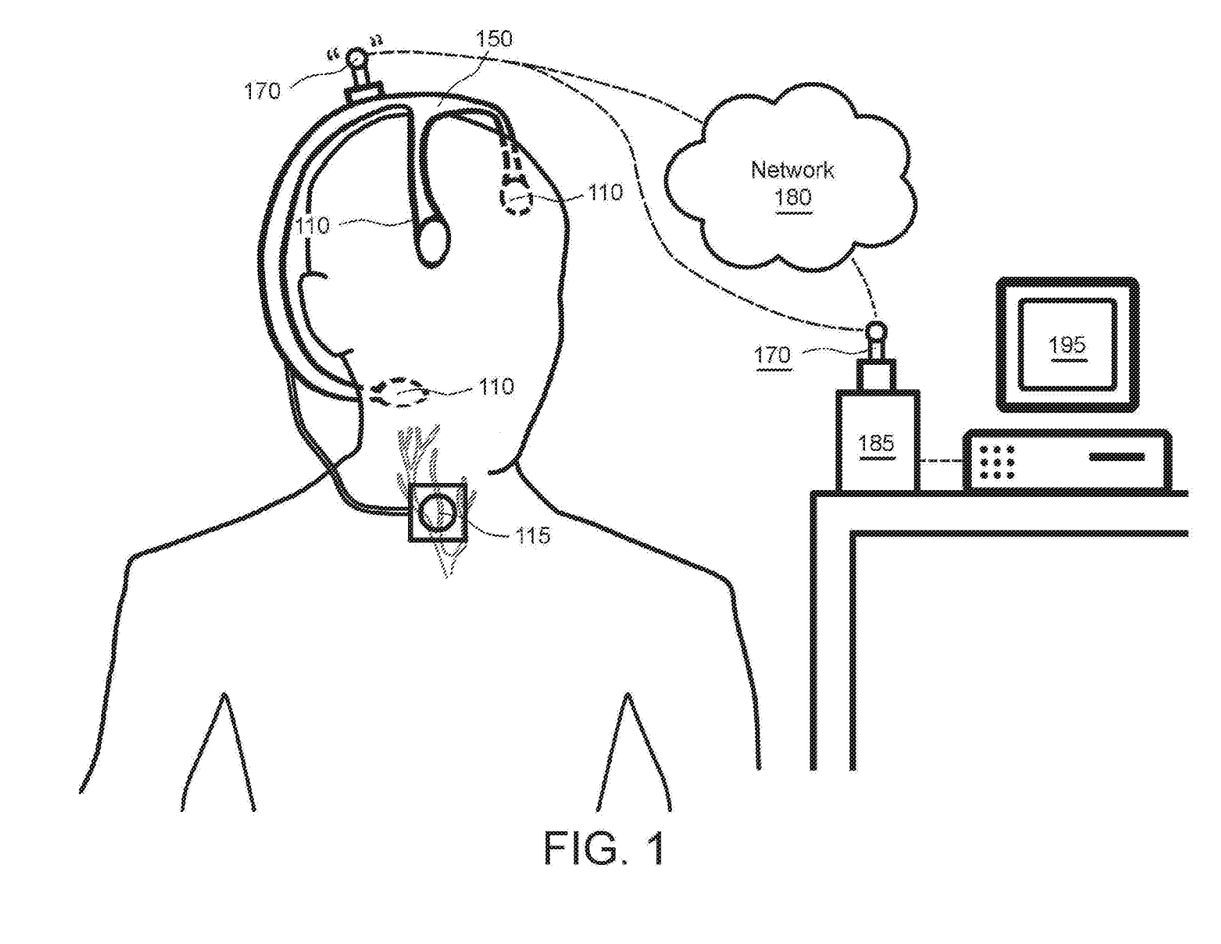
FIG. 1 depicts, in accordance with various embodiments of the present invention, an overview of a system for detecting brain pulsatility.

FIG. 1 illustrates an example system for monitoring a patient for brain injury. For instance, the system includes a headset 150 that includes ultrasound transducers 110 placed on the head, with two transducers 110 position on the temples, and one transducer 110 positioned to emit radiation through the foramen magnum. Also attached to the patient is a cardiovascular sensor 115 on the neck for detecting arterial waveforms emitted by the carotid artery.

The system may then detect these signals and either locally process them on the headgear 150 or send them to a signal processing unit 185 over antennas 170 (e.g. Bluetooth) for processing and optionally over a network 180. Then, the signals may be sent to computing device 195 for analysis or be analyzed using software and a control system on the processing unit 185.

The system may compare the measured pulsatility determined from the headgear 150 transducers, to the expected pulsatility derived from the cardiovascular sensor 115 that detect arterial waveforms. If there is a discrepancy between the measured and expected pulsatility, a notification may be sent to alert of the potential brain abnormality. Accordingly, now the components will be described in further detail.

Ultrasound Transducers

The ultrasound transducers 110 may be configured to emit and detect ultrasound into the brain of the patient. In some examples, they may be positioned on headgear 150 that can be applied to the patient. The headgear 150 may include a headband with wiring and patches to secure the transducers 110. In other examples, the transducers may be placed using adhesive patches, or other suitable techniques.

In some examples, each transducer 110 acts simultaneously as ultrasound emitting and receiving unit. In some examples, the three transducers 110 are synchronized and insonate the brain parenchyma with either continuous or intermittent pulse waves in the mega- or kilo-Hertz range.

In some examples, to generate three dimensional brain motion, the transducers 110 emit and receive impulses in predefined on-off sequences and constellations. The pulsating brain will shorten (compress) or lengthen (relax) the emitted ultrasound waves dependent on the direction of its movement relative to the transducer emission unit (Doppler effect). It is the degree of wave length and amplitude changes in the reflected waves which is extracted by the ultrasound processor and integrated to obtain graphic and numerical representations of brain motion.

In some examples, M-mode ultrasound will be utilized to obtain a very accurate picture of the orientation and magnitude of pulsatility. In other examples, 2 dimensional or other ultrasounds types may be utilized for more basic measures of brain movement. For instance, in some examples, a single transducer 110 may be placed on the temple, or foramen magnum, and a measure of the brain in one direction may be determined.

For example, a system developed by Spencer Technologies utilized a 2 MHz carrier frequency and an eight-cycle transmit burst emitted at a pulse-repetition frequency of 6.25 dHz which resulted in a one dimensional tissue displacement resolution of below a micron. The system was able to determine brain displacement along an axis of the emitted ultrasound at localized areas that were 4.5 mm intervals from the transducer to the other side of the brain. Accordingly, while this method provides some information about brain motion, it only provides information about brain displacement in one direction.

In other examples, one transducer 110 may be placed on each temple, or one transducer may be placed on one temple, and one transducer may be placed on the foramen magnum for a two dimensional displacement analysis. Various other configurations, and frequencies and combination of frequencies may be utilized as appropriate.

Cardiovascular Waveform Detector

FIG. 1 also illustrates a cardiovascular waveform detector 115. For instance, the cardiovascular waveform detector 115 may detect an arterial waveform associated with a pulse detected at the neck level of the carotid artery or the radial artery at the wrist. Accordingly, the transducer 115 may be a pressure transducer, or may be an acoustic transducer.

Figure 3:
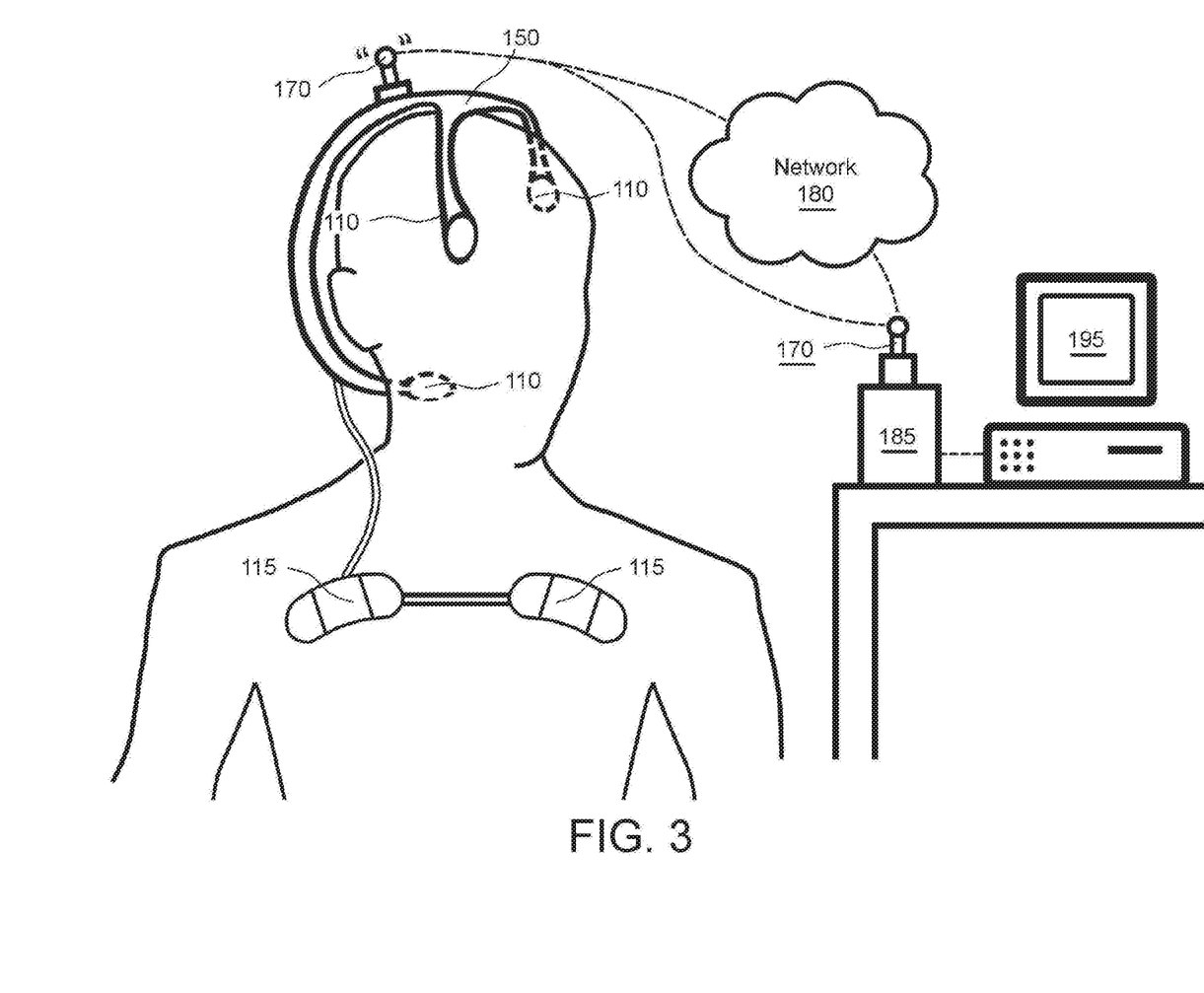
FIG. 3 depicts, in accordance with various embodiments of the present invention, an overview of a system for detecting brain pulsatility.
Figure 4:
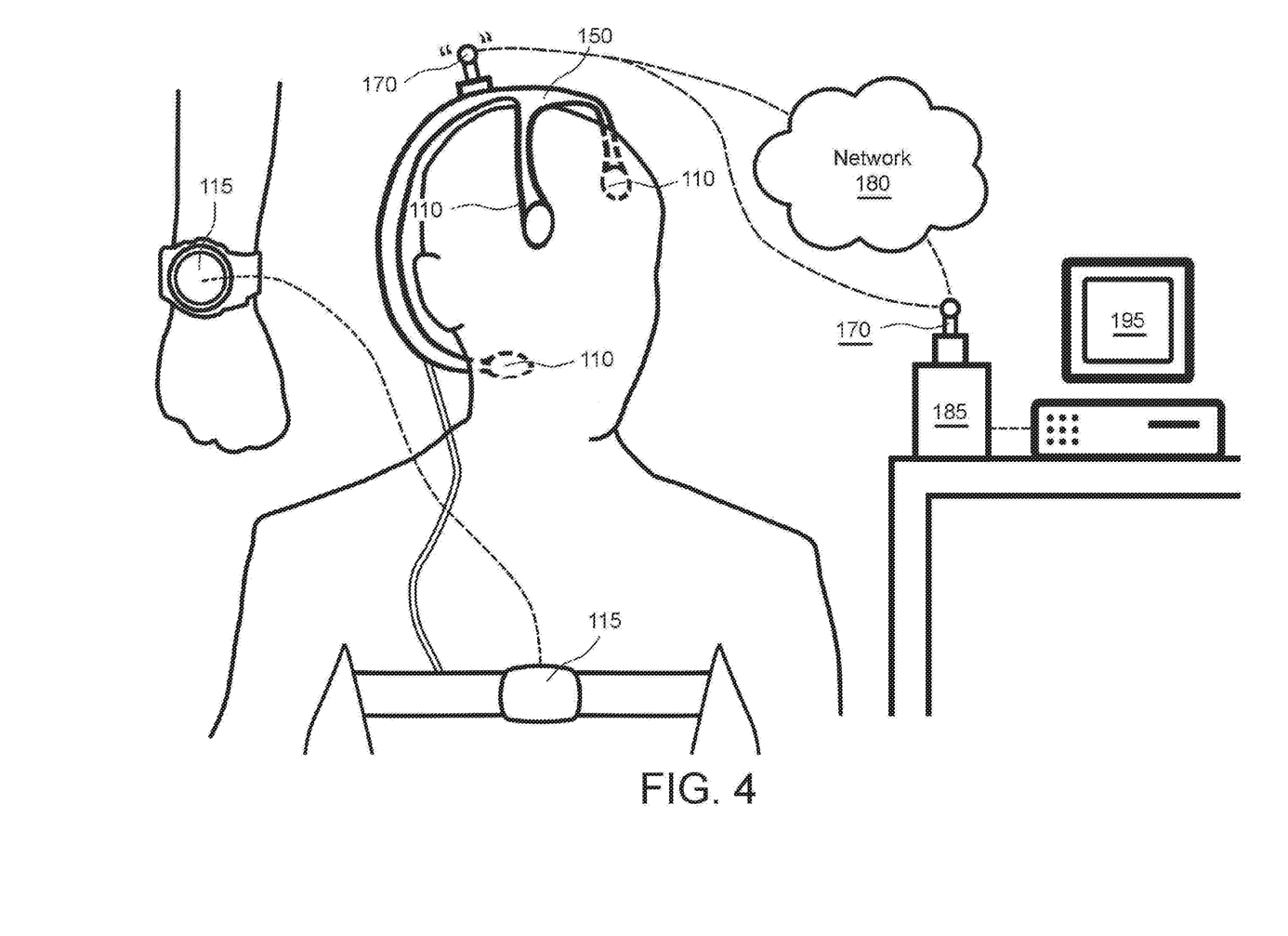
FIG. 4 depicts, in accordance with various embodiments of the present invention, an overview of a system for detecting brain pulsatility.

In some examples, as illustrated in FIG. 3, the cardiovascular waveform detector 115 may be an ECG or other device to detect the electrical signature of the heartbeat. In other examples, the cardiovascular waveform detector 115 may be a respiratory sensor as illustrated in FIG. 4 that includes a band around the chest that senses breathing.

Accordingly, the cardiovascular waveform detector 115 may be a variety of detectors that detect the cardiovascular cycles (e.g. heartbeat, breathing). In many examples, the cardiovascular detector 115 may be a detector that detect the cardiac cycle. For instance, the cardiac detector may be an ECG, EKG, pulse oximeter, or other cardiac cycle detector. In other examples, the respiratory cycle may be detected through various technologies.

In some examples, detection of the arterial pulse in the carotid artery may be advantageous because it is one of the least removed cardiac based pulsations prior to the blood entering the head. Accordingly, the lag between the pulsation of the arterial pulse may be less than the lag following the cardiac cycle. In other examples, better detail or magnitude information may be derived from detecting the cardiac pulse as opposed to sensing the arterial pulse in the carotid artery or other arteries.

In some examples, the arterial pulse of the arteries in the arm, wrist or legs may be utilized. Accordingly, various detectors 115 may be utilized in these different positions. The output of the detector 115 will then be processed to determine the timing of the cardiac cycle or other cardiovascular cycle being detected. This signal my then be compared to the pulsatility as disclosed herein.

Signal Processing Unit

The signal processing unit 185 may process signals from one or both of the detector 115 and the transducers 110 from the ultrasound unit. In some examples the ultrasound transducers 110 will have a signal processing unit 185 and the cardiovascular cycle detector 115 will have its only signal processing units 185. The signals from both sources will be subject to unique noise, interference, and have other processing requirement to identify the determined signal. Accordingly, the signal processing unit(s) 185 will have the appropriate amplifiers, filters, and other necessary signal processing capabilities.

In some examples, the signal processing unit 185 or a separate control unit may drive the ultrasound emissions, and accordingly supply control signals to the ultrasound transducers 110. In other examples, a separate driving and receiving unit may be included in the headgear or separately from the signal processing unit 185.

Processing Methods

Figure 2:
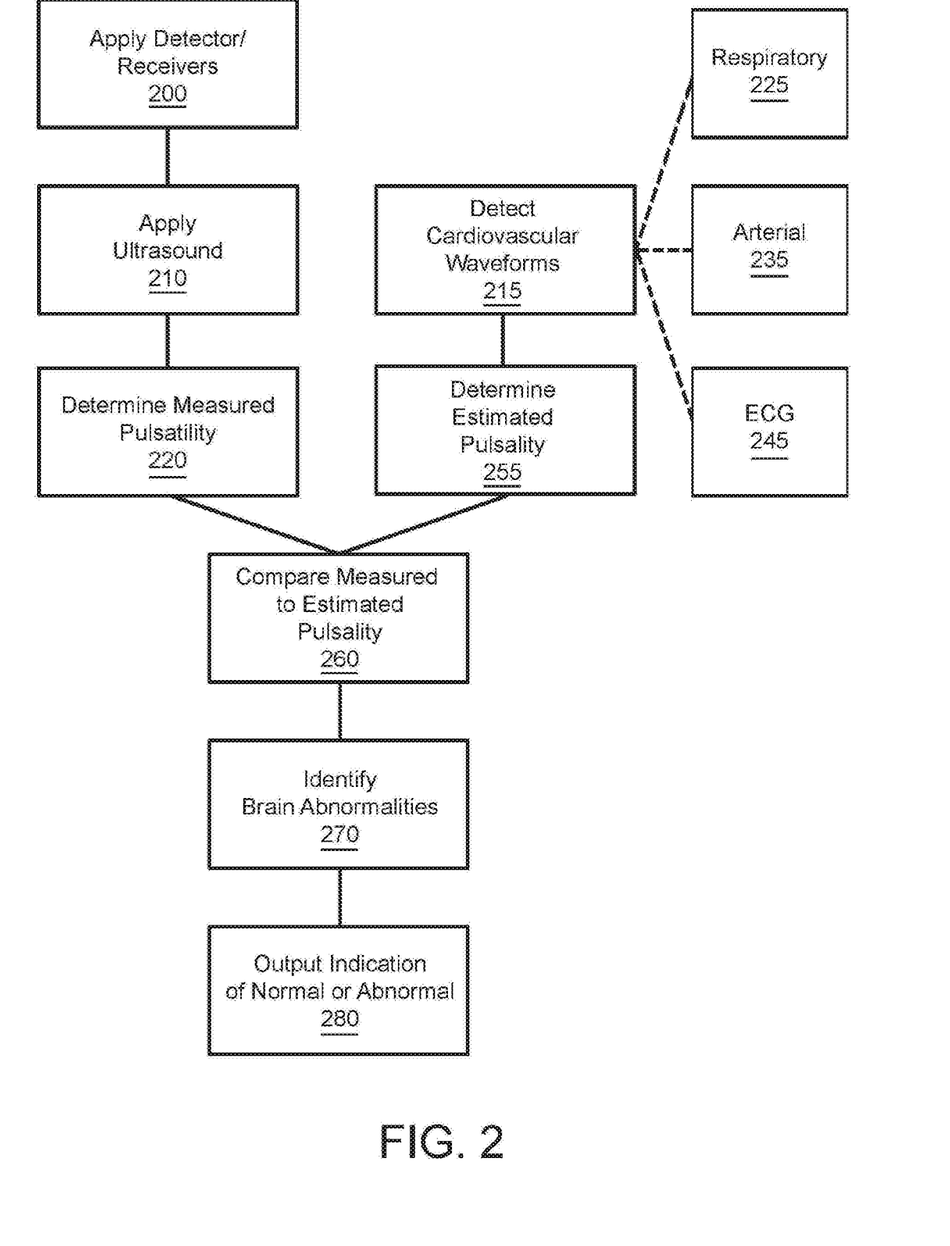
FIG. 2 depicts, in accordance with various embodiments of the present invention, a flow chart illustrating a process for detecting brain abnormalities using brain pulsatility.

FIG. 2 is a flow chart illustrating a processing for implementing the disclosed technology. For instance, a caregiver would first apply the detectors and receivers 200 (e.g. transducers 110) to the patient's head. In some examples, as discussed above, this may include positioning detectors in the bone windows. Then, the transducers 110 would be connected to a processing and driving unit that could drive the ultrasound frequencies, and detect the reflected sound waves.

Measured Pulsatility

After applying the transducers 200 or other emitters and detectors, the caregiver would initiate the ultrasound unit to begin to emit ultrasound frequencies from the transducers 110 and begin recording the reflected waives. After recording the ultrasound reflected waves, various algorithms would be utilized to determine the orientation and amount of movement in localized area of the brain. In some examples, this may include applying M-mode ultrasound and analyzing the information to determine movement of the brain. These movements would then be analyzed to determine pulsatility 220.

Pulsatility 220 could be determined based on a variety of factors and include different measures or different indexes for assessing different types of potential brain abnormalities. In some examples, these abnormalities can include traumatic brain injury or hydrocephalus that causes changes in pulsatile pressure, pulsatile waveforms, and pulsatile flow in the brain.

For instance, the brain pulsations are most pronounced as a cyclic downward (rostrocaudal) movement during systole. Accordingly, there may be a separate pulsatility measurement for this movement that detects changes in the direction of the pulsatility or the magnitude. Hydrocephalus, for example, may affect the magnitude of the displacement and traumatic brain injury may affect the direction of the motion. It has been shown that with increases in pressure, the pulsatile wave dramatically increases. See e.g., "The pulsating brain: A review of experimental and clinical studies of intracranial pulsatility".

Accordingly, different measures of the displacement may be recorded that include magnitudes of the pulsations on systole or other heart cycle related pulsations, or may include an average or moving window of average direction of the systole pulsation. In other examples, pulsatility could be a combined index that relates to a deviation from normal that includes both a magnitude and direction of pulsatility.

In other examples, the timing of the pulse wave will be recorded including the length or period of pulse wave. The more compliant the tissue in the brain is, the longer the pulsatile wave relative to a less compliant tissue. In other examples, pulse wave shape will be examined, including for examples the derivatives of pulse waves curves, for instance, in certain directions.

All of these measurements will include time stamp or other indications of time so that they can be compared to the estimated pulsatility. For instance, each reading may include a time stamp and each pulse wave, from the arterial, CSF and brain tissue compartments, may be temporally identified.

Estimated Pulsatility

Simultaneously while pulsatility is measured, a cardiovascular waveform detector(s) 115 may be applied to detect cardiovascular waveforms 215. For instance, the detector may be applied to various other portions of the body to detect the respiratory 225 or cardiac cycles (235 & 245), in some examples. For instance, an arterial waveform detector 235 may be applied to the neck to record the pulsations of the artery during systole of the cardiac cycle. In other examples, this may be an ECG detector 245, pulse oximeter, or other cardiac cycle detector 215.

A caregiver will attach the detector 115 and connect it to the headgear 150 or the processing unit 185 or other processing device to analyze the signals and identify the cardiac waveforms. For instance, the detector 115 may determine a time window or a time point for a beginning of an arterial pulsation that correlates to systole. This arterial pulsation may be time stamped so that it can be matched to pulsations in the brain recorded.

The brain and arterial pulsations may be matched by an expected time delay and waveform synchrony between detecting the arterial pulsation and receiving the brain pulsation. This will depend on the time of detector 115 and the position. For instance, if the detector detects pulsations on the carotid artery in the neck, the delay will be shorter than if an ECG is used to detect systole.

Additionally, the detector 115 may determine a relative measure of strength of the systole, so that the comparison between the estimated and measured pulsatility will be also based on the anticipated strength of the pulsatility. This may be determined by a magnitude of the ECG electrical signals detected during systole, a magnitude of pressure transducer information output from a detector 115, or the magnitude of the pulse wave detected by a pulse oximeter.

Next, the estimated pulsatility will be determined 255 based on the pulse wave detected by the cardiovascular detector 115. Accordingly, this may be based on experimental data from various healthy, age-grouped patients that have been monitored with the disclosed technology, or including based on past monitoring of a patient that will determine a deviation from the expected pulsatility that is beyond a threshold. Accordingly, the pulse wave detected (for example in the carotid artery) will result in a pulse wave detected in the brain.

The stronger the pulse wave in the carotid artery, the stronger the expected pulse wave would be in the brain. Therefore, the expected pulse wave will primarily be adjusted for the expected magnitude, in some examples, that is expected to result. Accordingly, deviations in magnitude that might otherwise be indicative of a brain abnormality may actually be detected as chances in strength of the cardiac systole. In some examples, the relative strength of the pulse detected in the artery will be used as a multiplier to determine the expected pulsatility or range pulsatility that will be considered normal in the brain.

Comparison of Measured to Expected Pulsatility

Next, the system may compare the measured to estimated pulsatility 260 in order to identify any abnormalities 270. For instance, in some examples, the estimated pulsatility 260 may be utilized to determine a normal range of pulsatility or move the range window around a certain magnitude.

In some examples the expected pulsatility may vary from the measured pulsatility by one or both of the magnitude and orientation of the brain pulsation during systole. Accordingly, the comparison may be on multiple factors, and a deviation in one of the factors may be correlated to a likelihood of specific abnormality.

For instance, deviations in the measured strength of pulsatility from the measured above a threshold may be flagged to check for certain brain injury types such as hydrocephalus. In other examples, deviation of the orientation of the wave may be flagged for other brain abnormalities, including brain trauma. Also, deviation of the length of the brain pulse may be related to abnormalities that impact the compliance of the brain tissue. Also, the degree of deviation or a deviation score may be derived for each measure that is useful for determining the likelihood of any abnormality.

Diagnosis Alerts

Once any abnormalities have been identified 270, the system may output various indications of the abnormalities 280. For instance, the disclosed technology may send an alert to a caregiver if any of the abnormalities indicate brain trauma, declining cerebral flow, increasing brain tissue density changes, hydrocephalus, and other conditions.

Additionally, the alerts could be calibrated for the degree of likelihood and potentially the degree of abnormality. Various alarms may be triggered if the abnormality is above a second threshold that indicates that abnormality is very likely and danger to the patient is imminent.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed.

Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A system for monitoring brain pulsatility to detect abnormalities, the system comprising:
    ultrasound transducers configured to be positioned on a head of the patient;
    a cardiovascular cycle detector;
    a memory containing machine readable medium comprising machine executable code having stored thereon instructions for performing a method of monitoring brain pulsatility; and
    a control system coupled to the memory, the control system configured to execute the machine executable code to cause the control system to:
        determine a measured movements and pulsatility of the brain based on signals output from the ultrasound transducers;
        determine an expected pulsatility of the brain based on signals output from the cardiovascular cycle detector;
        determine, by comparing the expected to measured pulsatility to an indication of likelihood of any potential brain abnormalities in the patient; and
        output the indication of likelihood of any potential brain abnormalities based on the comparison,
        wherein the comparison of the expected to measured pulsatility includes at least one comparison of the magnitude or direction of an expected to measured brain pulsation.

2. The system of claim 1, wherein the signals output from the ultrasound transducers are based on M-Mode ultrasound.

3. The system of claim 1, wherein the cardiovascular cycle detector is a pressure transducer.

4. The system of claim 1, wherein the cardiovascular cycle detector is an ECG system.

5. The system of claim 1, wherein the cardiovascular cycle detector is a pulse oximeter.

6. The system of claim 1 further includes a headset, wherein the headset includes at least two ultrasound transducers configured to be positioned on the temples of the patient, and one ultrasound transducer configured to be positioned on the foramen magnum of the patient.

7. The system of claim 1, wherein the measured pulsatility includes an orientation and magnitude of pulsatility.

8. The system of claim 1, wherein the measured pulsatility includes a length of period of a brain pulsation.

9. The system of claim 1, wherein the expected pulsatility is a range of expected pulsatility calculated based on the magnitude of the pulsation detected by the cardiovascular cycle detector.

10. The system of claim 1, wherein the indication is an alert if the measured pulsatility is outside a predetermined threshold of expected pulsatility.

11. The system of claim 1, wherein the comparison of the measured pulsatility includes separate comparisons of the magnitude, direction, delay and period length of an expected to measured brain pulsation.

12. The system of claim 11, wherein the magnitude of the difference determined by at least one of the comparisons is used to determine a likelihood of hydrocephalus or brain injury.

13. The system of claim 1, wherein the ultrasound transducers comprise at least two ultrasound transducers configured to be positioned on the temples, and one ultrasound transducer configured to be positioned on the foramen magnum.

14. The system of claim 1, wherein the ultrasound transducers comprise at least one ultrasound transducer configured to be positioned over the vertex, fontanelle, or other areas of skull bone.

15. A method for monitoring brain pulsatility to detect abnormalities in a patient's brain, the method comprising:
receiving, from ultrasound transducers, ultrasound data based on M-mode ultrasound waves reflected from a brain of a patient;
determining, by a processor, a measured pulsatility of the brain based on the ultrasound data;
receiving, from a cardiovascular cycle detector, cardiovascular cycle data;
determining, by the processor, an expected pulsatility of the brain based on the cardiovascular cycle data;
determining, by comparing the expected to measured pulsatility of the brain to an indication of likelihood of any potential brain abnormalities in the patient; and
outputting the indication of likelihood of any potential brain abnormalities based on the comparison,
wherein the comparison of the expected to measured pulsatility includes at least one comparison of the magnitude or direction of an expected to measured brain pulsation.

16. The method of claim 15, wherein the comparing further comprises matching a pulsation wave detected by the cardiovascular cycle detector to a brain pulsation wave based on a time delay, synchronicity and amplitude spectrum.

17. The method of claim 15, wherein the determining an expected pulsatility further comprises determining an average pulsation wave detected in a pre-defined time window by the cardiovascular cycle detector.

18. The method of claim 17, wherein the determining a measured pulsatility further comprises determining an average pulsation wave detected in a pre-defined time window by the ultrasound transducers.

19. The method of claim 18, wherein the comparing further comprises comparing the average expected pulsatility to the average measured pulsatility.

* * * * *